(12) United States Patent
Marshall et al.

(10) Patent No.: US 8,612,245 B2
(45) Date of Patent: Dec. 17, 2013

(54) PERSONALIZED HEALTH HISTORY SYSTEM WITH ACCOMMODATION FOR CONSUMER HEALTH TERMINOLOGY

(75) Inventors: Philip D. Marshall, Portland, OR (US); Bradley R Bowman, Tigard, OR (US); Michael J. Rozen, Palm Beach Gardens, FL (US)

(73) Assignee: WebMD LLC, New York, NY (US)

( * ) Notice: Subject to any disclaimer, the term of this patent is extended or adjusted under 35 U.S.C. 154(b) by 1283 days.

(21) Appl. No.: 10/654,503

(22) Filed: Sep. 3, 2003

(65) Prior Publication Data

US 2004/0044548 A1    Mar. 4, 2004

Related U.S. Application Data

(63) Continuation of application No. 09/512,231, filed on Feb. 24, 2000, now abandoned.

(51) Int. Cl.
    *G06Q 10/00* (2012.01)
(52) U.S. Cl.
    USPC .................................................. 705/2; 705/3
(58) Field of Classification Search
    USPC .......................................................... 705/2, 3
    See application file for complete search history.

(56) References Cited

U.S. PATENT DOCUMENTS

| | | | |
|---|---|---|---|
| 4,315,309 A | 2/1982 | Coli | 705/3 |
| 4,812,994 A | 3/1989 | Taylor et al. | 705/410 |
| 4,858,121 A | 8/1989 | Barber et al. | 705/2 |
| 4,868,376 A | 9/1989 | Lessin et al. | 235/492 |
| 4,882,474 A | 11/1989 | Anderl et al. | 235/380 |
| 4,916,611 A | 4/1990 | Doyle, Jr. et al. | 705/2 |
| 4,949,251 A | 8/1990 | Griffin et al. | 714/20 |
| 4,960,982 A | 10/1990 | Takahira | 235/382 |
| 4,984,272 A | 1/1991 | McIlroy et al. | 713/202 |
| 5,150,409 A | 9/1992 | Elsner | 713/177 |
| 5,241,671 A | 8/1993 | Reed et al. | 707/104.1 |
| 5,251,152 A | 10/1993 | Notess | 709/224 |
| 5,301,105 A | 4/1994 | Cummings, Jr. | 705/2 |
| 5,301,246 A | 4/1994 | Archibald et al. | 379/142.06 |
| 5,325,294 A | 6/1994 | Keene | 705/3 |
| 5,327,341 A | 7/1994 | Whalen et al. | 705/3 |
| 5,430,875 A | 7/1995 | Ma | 719/318 |

(Continued)

OTHER PUBLICATIONS

Yuri Quintana, Intelligent Medical Information Filtering, International Journal of Medical Informatics, 1998.*

(Continued)

*Primary Examiner* — Lena Najarian
(74) *Attorney, Agent, or Firm* — Wilmer Cutler Pickering Hale and Dorr LLP

(57) ABSTRACT

Personalization of access to health-related information on a computer network is provided based upon a health history of a user. In one implementation, personal health-related information about the user is obtaining from the user operating a client computer. The health-related information includes one or more health-related terms that each corresponds to a health-related concept. The health related terms provided by the user are correlated with a health terminology thesaurus that is stored on a computer-readable medium, such as at a server remote from the user client. Each of the health-related terms is associated with a single concept unique identifier that uniquely identifies a corresponding health-related concept. Health-related works or content is made accessible over the computer network by correlating the concept unique identifiers for the user's health information with corresponding concept unique identifiers that are associated with the health-related content.

17 Claims, 3 Drawing Sheets

(56) References Cited

U.S. PATENT DOCUMENTS

| | | | | |
|---|---|---|---|---|
| 5,465,082 | A | 11/1995 | Chaco | 340/825.49 |
| 5,491,800 | A | 2/1996 | Goldsmith et al. | 709/221 |
| 5,517,405 | A * | 5/1996 | McAndrew et al. | 706/45 |
| 5,550,971 | A | 8/1996 | Brunner et al. | 395/161 |
| 5,559,885 | A | 9/1996 | Drexler et al. | 235/380 |
| 5,559,888 | A | 9/1996 | Jain et al. | 380/25 |
| 5,560,008 | A | 9/1996 | Johnson et al. | 713/201 |
| 5,572,422 | A | 11/1996 | Nematbakhsh et al. | 705/3 |
| 5,588,148 | A | 12/1996 | Landis et al. | 707/1 |
| 5,629,981 | A | 5/1997 | Nerlikar | 713/168 |
| 5,664,109 | A | 9/1997 | Johnson et al. | 705/2 |
| 5,664,207 | A | 9/1997 | Crumpler et al. | 715/505 |
| 5,742,816 | A * | 4/1998 | Barr et al. | 707/3 |
| 5,772,585 | A | 6/1998 | Lavin et al. | 600/300 |
| 5,790,785 | A | 8/1998 | Klug et al. | 713/202 |
| 5,809,476 | A | 9/1998 | Ryan | 705/2 |
| 5,815,665 | A | 9/1998 | Teper et al. | 709/229 |
| 5,827,180 | A | 10/1998 | Goodman | 600/300 |
| 5,832,488 | A | 11/1998 | Eberhardt | 707/10 |
| 5,841,970 | A | 11/1998 | Tabuki | 713/201 |
| 5,845,255 | A | 12/1998 | Mayaud | 705/3 |
| 5,848,397 | A | 12/1998 | Marsh et al. | 705/14 |
| 5,857,190 | A | 1/1999 | Brown | 707/10 |
| 5,862,327 | A | 1/1999 | Kwang et al. | 709/203 |
| 5,867,821 | A | 2/1999 | Ballantyne et al. | 705/2 |
| 5,903,889 | A | 5/1999 | De la Huerga et al. | 707/3 |
| 5,905,884 | A | 5/1999 | Williams | 709/227 |
| 5,915,240 | A * | 6/1999 | Karpf | 705/2 |
| 5,926,811 | A * | 7/1999 | Miller et al. | 707/5 |
| 5,953,704 | A | 9/1999 | McIlroy et al. | 705/2 |
| 5,960,403 | A | 9/1999 | Brown | 705/2 |
| 5,967,789 | A | 10/1999 | Segel et al. | 434/236 |
| 5,974,412 | A | 10/1999 | Hazlehurst et al. | 707/3 |
| 5,978,842 | A | 11/1999 | Noble et al. | 709/218 |
| 5,996,715 | A | 12/1999 | Peay et al. | 707/203 |
| 6,006,269 | A | 12/1999 | Phaal | 709/227 |
| 6,018,619 | A | 1/2000 | Allard et al. | 709/224 |
| 6,031,818 | A | 2/2000 | Lo et al. | 370/216 |
| 6,047,327 | A * | 4/2000 | Tso et al. | 709/232 |
| 6,070,160 | A | 5/2000 | Geary | 707/4 |
| 6,073,106 | A | 6/2000 | Rosen et al. | 705/3 |
| 6,073,163 | A | 6/2000 | Clark et al. | 709/203 |
| 6,076,166 | A * | 6/2000 | Moshfeghi et al. | 726/4 |
| 6,092,196 | A | 7/2000 | Reiche | 713/200 |
| 6,112,183 | A | 8/2000 | Swanson et al. | 705/2 |
| 6,141,759 | A | 10/2000 | Braddy | 713/201 |
| 6,167,523 | A | 12/2000 | Strong | 713/201 |
| 6,178,416 | B1 * | 1/2001 | Thompson et al. | 707/3 |
| 6,189,036 | B1 | 2/2001 | Kao | 709/229 |
| 6,253,228 | B1 | 6/2001 | Ferris et al. | 709/203 |
| 6,263,330 | B1 | 7/2001 | Bessette | 707/4 |
| 6,289,353 | B1 * | 9/2001 | Hazlehurst et al. | 707/102 |
| 6,292,796 | B1 * | 9/2001 | Drucker et al. | 707/5 |
| 6,334,778 | B1 | 1/2002 | Brown | 273/429 |
| 6,347,374 | B1 | 2/2002 | Drake et al. | 713/200 |
| 6,362,836 | B1 | 3/2002 | Shaw et al. | 345/744 |
| 6,366,956 | B1 * | 4/2002 | Krishnan | 709/223 |
| 6,385,611 | B1 | 5/2002 | Cardona | 707/6 |
| 6,401,072 | B1 | 6/2002 | Haudenschild et al. | 705/3 |
| 6,449,598 | B1 | 9/2002 | Green et al. | 705/2 |
| 6,505,196 | B2 * | 1/2003 | Drucker et al. | 707/5 |
| 6,581,038 | B1 * | 6/2003 | Mahran | 705/3 |
| 6,584,445 | B2 * | 6/2003 | Papageorge | 705/3 |
| 6,738,754 | B1 * | 5/2004 | Norman, Jr. | 707/2 |
| 6,826,696 | B1 | 11/2004 | Chawla et al. | 713/201 |
| 6,904,408 | B1 * | 6/2005 | McCarthy et al. | 705/2 |
| 7,020,618 | B1 * | 3/2006 | Ward | 705/8 |
| 2001/0021910 | A1 * | 9/2001 | Goldstein | 705/2 |
| 2002/0165737 | A1 * | 11/2002 | Mahran | 705/3 |

OTHER PUBLICATIONS

William M. Detmer, G. Octo Barnett, and William R. Hersh, MedWeaver: Integrating Decision Support, Literature Searching, and Web Exploration using the UMLS Metathesaurus, 1997.*

Yuri Quintana, User Modelling and Information Filtering for Consumer Information, New Media Lab, IEEE, 1997.*

\* cited by examiner

PERSONALIZED HEALTH HISTORY SYSTEM WITH ACCOMMODATION FOR CONSUMER HEALTH TERMINOLOGY

This application is a continuation of U.S. patent application Ser. No. 09/512,231, filed Feb. 24, 2000, now abandoned entitled PERSONALIZED HEALTH HISTORY SYSTEM WITH ACCOMMODATION FOR CONSUMER HEALTH TERMINOLOGY, which is hereby incorporated by reference in its entirety for each of its teachings and embodiments.

FIELD OF THE INVENTION

The present invention relates to providing personalized access to content that is available over a computer network and, in particular, to providing health-related content that is accurately personalized according to personal health information about the user, including health information that is described in lay medical terminology.

BACKGROUND AND SUMMARY OF THE INVENTION

Consumer health information is growing in importance and popularity, with computer networks such as the Internet providing a growing share of the information. It is estimated that health issues are addressed at tens of thousands of online sites with potentially millions of pages of health-related works or content. With a general lack of clinical and editorial standards for health-related content, lay consumers without specific medical training, and even trained medical professionals, can have relatively little success in finding desired or relevant information among such vast resources.

Moreover, given the extremely personal nature of health, most individuals have minimal interest in browsing materials that have no relevance to their health or the health of their families. Yet most of the health information available at conventional network (e.g., Internet) sites or portals addresses only general topics. Such information seldom has any particular relevance to individual users. Accordingly, there is a need for an improved way of obtaining relevant or personalized health-related content from computer networks such as the Internet.

Conventional network (e.g., Internet) systems employ a variety of personalization processes that at least minimally personalize a network site for different visitors or users. The personalization provided by many such processes is relatively simplistic and provides personalization only to the extent of a small number of personalization options. These conventional personalization processes include Greetings, which can be as simple as providing a "welcome sign" that informs the user of the state of a single condition, such as, "Hello you've got mail;" Pick Lists, which allow users to select from predetermined lists of news categories, horoscopes, sports scores, etc.; Keywords, codes or symbols, which can be referenced by entering keywords such as zip codes for local weather forecasts or stock ticker symbols for stock quotes; Demographic/traffic analysis, which is usually derived from a log file which indicates a user's name, email address, zip code, and Internet Service Provider information; Comparison methods, which use data provided by other users to highlight similarities and differences among users; and Collaborative processes, which select content or works based on the preferences of others who are in some way similar to the user.

Personalization processes in use today, including the use of demographics and pick-lists, are inadequate for the vast amounts of health-related information and the relatively narrow interests of many users. Pick Lists are useful, when the possible selections number fewer than several (e.g., 4 or 5) dozens. However, health related content can be usefully categorized among hundreds or thousands of distinct topics. As a consequence, conventional health-related network sites that employ Pick Lists for personalization typically provide relatively few selections that each cover broad areas of information. Such broad coverage areas render such personalization ineffective for the specific health-related information desired by many users.

The present invention provides personalization of access to health-related content on a computer network based upon a health history of a user. In one implementation, personal health-related information about the user is obtained from a user operating a client computer. The health-related information includes one or more health-related terms that each corresponds to a health-related concept. The personal health information may relate to health conditions, which may include medical diagnoses like diabetes, high blood pressure, pneumonia, or pregnancy, or any current or past health problems like poor vision, chronic joint pain, cancer, or alcoholism. The health information could also or alternatively relate to allergies, tests, vaccinations, surgeries or procedures, etc. that affect or have affected the health of the user or that are a part of the user's health history.

The health related terms provided by the user are correlated with a health terminology thesaurus that is stored on a computer-readable medium, such as at a server remote from the user client. Each of the health-related terms is associated with a single concept unique identifier that uniquely identifies a corresponding health-related concept. Each concept unique identifier has associated with it one or more terms corresponding to a common health-related concept. Some of the terms are clinical medical terms and others are lay medical terms that are not clinical medical terms.

Health-related works or content that is accessible over a computer network may be identified in a personalized manner based upon the concept unique identifiers. The health-related content may include, for example, health news, product and service information, disease information, medication information, and other health-related content. Each health-related work has associated with it one or more concept unique identifiers. Personalized identification of the health-related works entails matching the concept unique identifiers of the terms provided by the user with the concept unique identifiers of works relating to those terms. In addition, the Concept Unique Identifier is related to other Concept Unique Identifiers to give it greater semantic meaning and context. The relationships of concepts are derived from existing professional healthcare vocabularies, including Snomed, Medical Subject Headings, and International Classification of Diseases. These relationships allow the term "type 2 sugar disease" which equates to the concept of adult-onset diabetes mellitus, to be related as a narrower concept to diabetes mellitus, which in turn is a narrower concept than diabetes, which in turn is a narrower concept to endocrine and glandular disorders. This then allows an article written simply about "Diabetes" to find all those who would benefit from this information, including those who described themselves as having "type 2 sugar disease."

The present invention provides personalized access to health-related information that can accommodate the particular interests of both professional and lay users and the vast amounts of and conflicting terminology in health-related information. In contrast, conventional personalization processes are inadequate for the particularized interests of users in combination with the vast and complex resources of health-related information.

Additional objects and advantages of the present invention will be apparent from the detailed description of the preferred embodiment thereof, which proceeds with reference to the accompanying drawings.

DETAILED DESCRIPTION OF PREFERRED EMBODIMENTS

Figure 1:
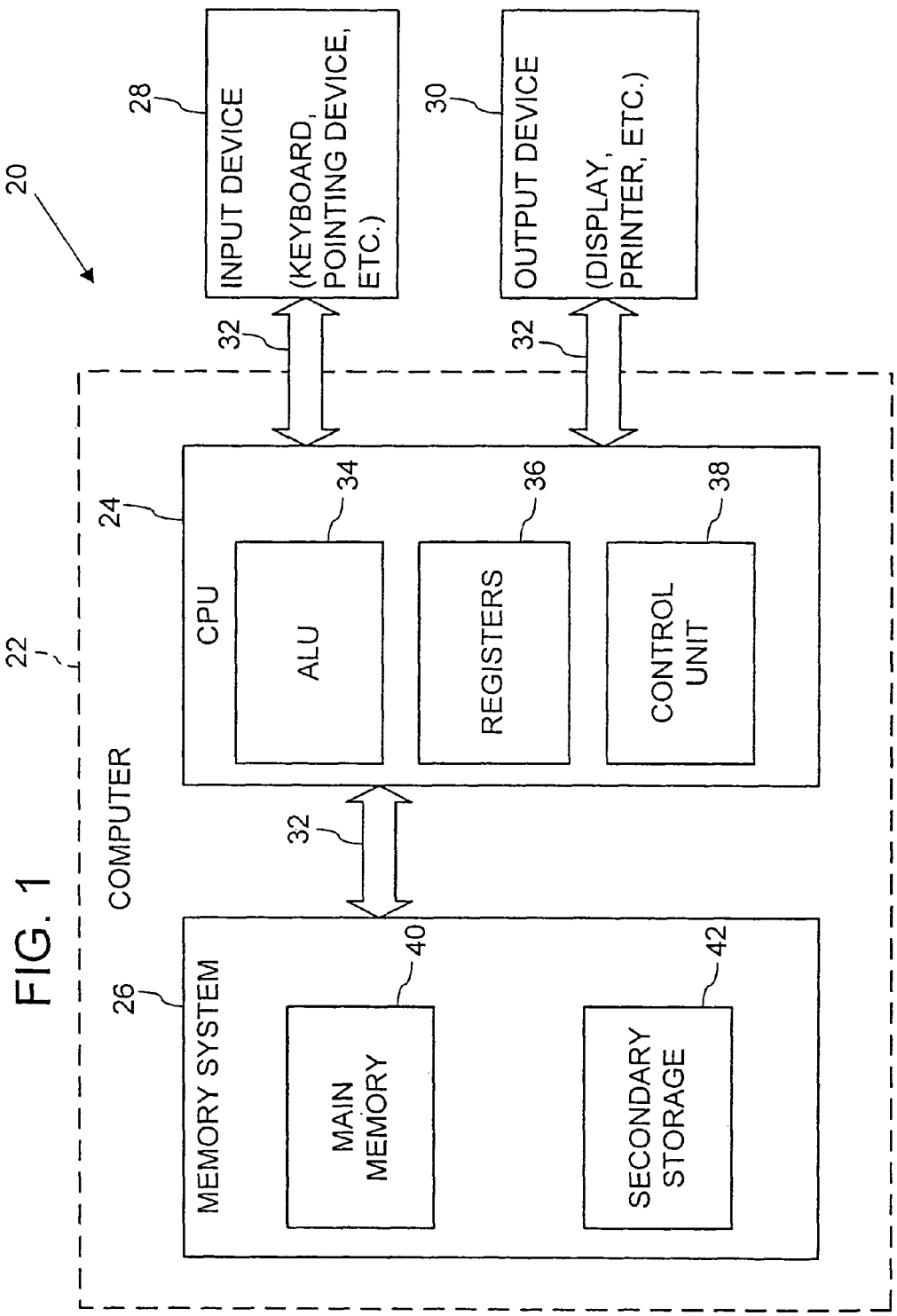
FIG. 1 is a block diagram of a computer system that may be used to implement the present invention.

FIG. 1 illustrates an operating environment for an embodiment of the present invention as a computer system 20 with a computer 22 that comprises at least one high speed processing unit (CPU) 24 in conjunction with a memory system 26, an input device 28, and an output device 30. These elements are interconnected by at least one bus structure 32.

The illustrated CPU 24 is of familiar design and includes an ALU 34 for performing computations, a collection of registers 36 for temporary storage of data and instructions, and a control unit 38 for controlling operation of the system 20. The CPU 24 may be a processor having any of a variety of architectures including Alpha from Digital, MIPS from MIPS Technology, NEC, IDT, Siemens, and others, x86 from Intel and others, including Cyrix, AMD, and Nexgen, and the PowerPC from IBM and Motorola.

The memory system 26 generally includes high-speed main memory 40 in the form of a medium such as random access memory (RAM) and read only memory (ROM) semiconductor devices, and secondary storage 42 in the form of long term storage mediums such as floppy disks, hard disks, tape, CD-ROM, flash memory, etc. and other devices that store data using electrical, magnetic, optical or other recording media. The main memory 40 also can include video display memory for displaying images through a display device. Those skilled in the art will recognize that the memory 26 can comprise a variety of alternative components having a variety of storage capacities.

The input and output devices 28 and 30 also are familiar. The input device 28 can comprise a keyboard, a mouse, a physical transducer (e.g., a microphone), etc. The output device 30 can comprise a display, a printer, a transducer (e.g., a speaker), etc. Some devices, such as a network interface or a modem, can be used as input and/or output devices.

As is familiar to those skilled in the art, the computer system 20 further includes an operating system and at least one application program. The operating system is the set of software which controls the computer system's operation and the allocation of resources. The application program is the set of software that performs a task desired by the user, using computer resources made available through the operating system. Both are resident in the illustrated memory system 26.

In accordance with the practices of persons skilled in the art of computer programming, the present invention is described below with reference to acts and symbolic representations of operations that are performed by computer system 20, unless indicated otherwise. Such acts and operations are sometimes referred to as being computer-executed and may be associated with the operating system or the application program as appropriate. It will be appreciated that the acts and symbolically represented operations include the manipulation by the CPU 24 of electrical signals representing data bits which causes a resulting transformation or reduction of the electrical signal representation, and the maintenance of data bits at memory locations in memory system 26 to thereby reconfigure or otherwise alter the computer system's operation, as well as other processing of signals. The memory locations where data bits are maintained are physical locations that have particular electrical, magnetic, or optical properties corresponding to the data bits.

Figure 2:
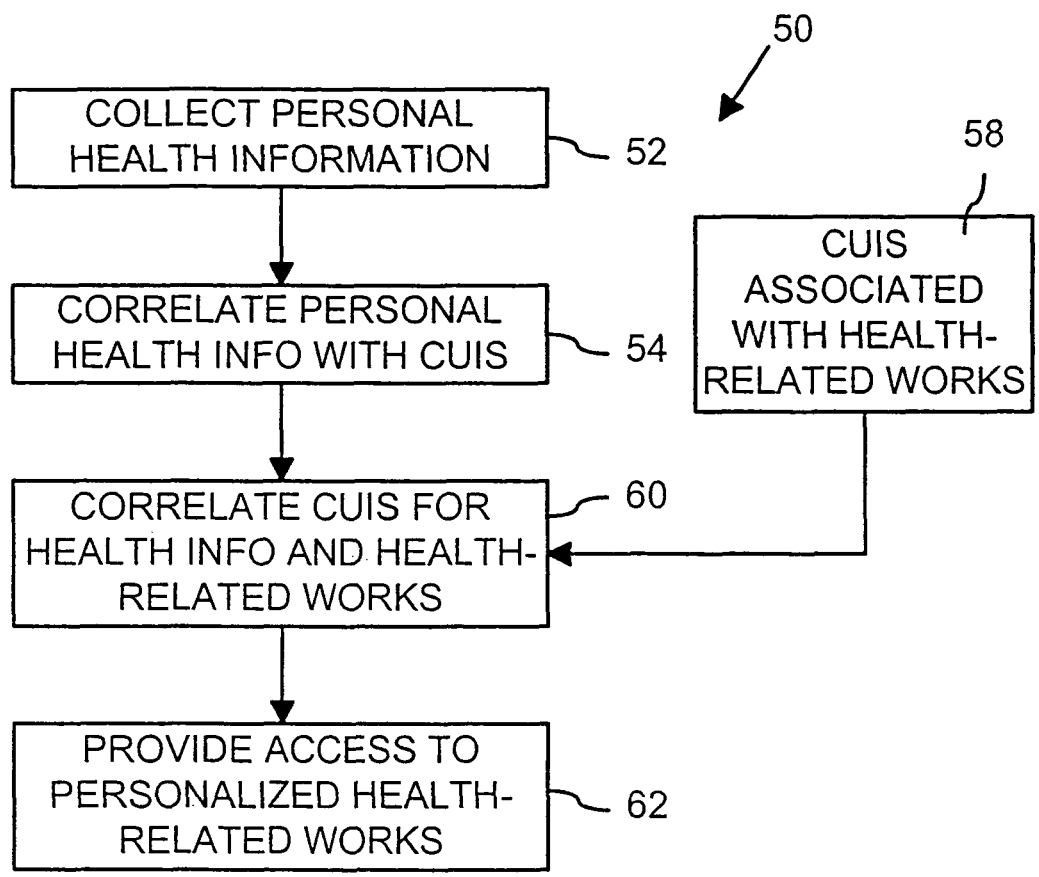
FIG. 2 is a flow diagram of a health history personalization process.

FIG. 2 is a flow diagram of a health history personalization process 50 for personalizing health-related content that is accessible by a user at a network-connected computer, the user commonly being a lay individual without specific medical training. The computer network may be private or public and may be a local area network or a wide area network. In one implementation, health history personalization process 50 operates and access to the health-related content are provided to the user over the Internet.

Process block 52 indicates that personal health information is collected about the user. The personal health information may relate to health conditions, which may include medical diagnoses like diabetes, high blood pressure, pneumonia, or pregnancy, or any current or past health problem like poor vision, chronic joint pain, cancer, or alcoholism.

Alternatively, the health information could relate to allergies, tests, vaccinations, surgeries or procedures, etc. that affect or have affected the health of the user or that are a part of the user's health history. For purposes of explanation, the following description is made with reference to the health information relating to health conditions. It will be appreciated that the description is similarly applicable to other types of health information, including information relating to allergies, tests, vaccinations, surgeries or procedures, etc.

Process block 54 indicates that the personal health information are correlated with predefined concept unique identifiers (CUIs). Each concept unique identifier uniquely identifies a predefined health-related concept (e.g., a health condition). The concept unique identifiers provide standardized identification of the predefined health-related concepts independent of traditional variations between lay medical and clinical medical terminology for health conditions, as described below in greater detail. In one implementation, the concept unique identifiers are in the form of alpha-numeric segments (e.g., 8 characters each). Alternatively, numeric or alphabetic segments could be used.

The concept unique identifiers are based on core medical concepts, enabling multiple synonyms and related terms to be mapped to the same concept unique identifier or code. For example, "hyperpeisis," "elevated systolic pressure," "high blood pressure," "hypertensive vascular disease" and "high blood" are all used in consumer and professional circles to describe the same thing: high blood pressure. Accordingly, all these terms would be mapped or associated with a single concept unique identifier.

Process block 58 indicates that one or more concept unique identifiers are associated with each of many health-related works or content (e.g., health news, product and service information, disease information, medication information, and other health-related content that are available over the network) that relate to the predefined health-related concepts corresponding to the concept unique identifiers. The associations between the health-related content and the concept unique identifiers are maintained in a database as a data structure on a computer-readable medium.

In addition to the association of concept unique identifiers pertaining to the subject of the health related works, a combination of concept unique identifiers is associated with the health related works to identify the appropriate populations of users for whom the health-related work are most appropriate. Additive concept unique identifiers are used to identify populations of appropriate users, such as male, age 40-60, history of prostate cancer, on the medicine Lupron, and on the medicine Aspirin. Exclusion of concepts from the target population of users is also performed, such as the above criteria, but excluding users who are on the medicine Proscar.

As another example for how the system can utilize a combination of concept unique identifiers and excluded concept unique identifiers to define populations of appropriate recipients for health-related works, the association of subject-based concept unique identifiers to a news article entitled "Exercise found to reduce the risk for breast cancer" will result in the concept unique identifiers for breast cancer, breast cancer prevention, and exercise. This article then is also indexed with a combination of concept unique identifiers (additive and/or excluded) for which the article is most appropriate. For example, the above mentioned article would be "targeted" to women between the ages of 30 and 70 who are at risk for breast cancer but who have not had a history of breast cancer.

Process block 60 indicates that the concept unique identifiers for the personal health information collected about the user are correlated with the concept unique identifiers of health-related content available over the computer network to identify health-related content that is personalized for the user.

Process block 62 indicates that access to the personalized health-related content is provided to the user. It will be appreciated that the access to the content may be provided to the user in a number of ways. For example, the personalized health-related content may be provided as personalized hyperlinks that are selectable by the user or the content itself may be provided directly to the user. The access to the personalized health-related content may be provided to the user in several ways. For example, the access to the content may be "pushed" to the user without a specific request by the user for the information, but rather based upon the personal health information provided by the user. As another example, the access to the information may be provided to the user in response to a specific request or search by the user.

Exemplary concept unique identifiers and corresponding predefined health-related concepts or terms for several health conditions are listed below in Table 1. The relationship between each concept unique identifier and the corresponding health-related term or terms forms a data structure that is stored in a computer-readable medium and includes a concept unique identifier (e.g., alphanumeric) and one or more associated health-related terms. The data structure allows uniform identification of health-related concepts despite a variety of lay medical terms and clinical medical terms being in use. The listing of Table 1 is not exhaustive of the health condition medical terms to which the concept unique identifiers may be applied.

TABLE 1

| Clinical Medical Term or Terms | Lay Medical Term | CUI |
| --- | --- | --- |
| guarding of the abdomen-involuntary | abdomen sensitive to touch | C0238547 |

TABLE 1-continued

| Clinical Medical Term or Terms | Lay Medical Term | CUI |
| --- | --- | --- |
| nipple discharge, abnormal | abnormal nipple discharge | C0149741 |
| adrenalin-test | adrenalin level | C0201998 |
| aminophylline, serum | aminophylline level | C0002575 |
| amitriptyline, serum | amitriptyline level | C0202316 |
| ammonia-test | ammonia level | C0201879 |
| salicylate, serum | aspirin level | C0202463 |
| congenital band syndrome | baby bands | C0220724 |
| urination, bed wetting | bed wetting | C0014394 |
| oropharynx lesion biopsy | biopsy of throat | C0192211 |
| periods, menstrual-bleeding between | bleeding between menstrual periods | C0302811 |
| ear discharges/bleeding | bleeding from ear | C0271412 |
| HCG (qualitative-serum) | blood HCG level | C0430064 |
| hemoglobin; serum | blood hemoglobin level | C0523685 |
| lead-serum | blood lead level | C0524167 |
| lithium, serum | blood lithium level | C0337452 |
| born with an optic disc abnormality | born with an abnormal optic nerve | C0521571 |
| tachypnea | breathing fast | C0231835 |
| backbone fracture | broken back | C0080179 |
| metacarpal fracture | broken metacarpal | C0272677 |
| sacrum/coccyx fracture | broken tailbone | C0149860 |
| monoplegia of lower extremity | can't move leg | C0154702 |
| dysuria | pain with urination | C0028961 |
| vision, night blindness | can't see at night | C0028077 |
| inability to sleep | can't sleep | C0021603 |
| smell, impaired | can't smell | C0481703 |
| median nerve release | carpal tunnel surgery | C0196576 |
| hoarseness or changing voice | changing voice | C0518179 |
| chest laceration | chest cut | C0432951 |
| Hiccups, Chronic | chronic hiccups | C0019521 |
| chronic pain and fatigue condition | chronic pain | C0150055 |
| diuretic | water pill | C0033231 |
| hydroxyzine injection | cortisone shot | C0010137 |
| computerized tomography of orbit | CT of eye socket | C0202754 |
| CXR | Chest XRay | C0202783 |
| Fracture | broken | C0016658 |
| Diabetes mellitus | Sugar disease | C0011849 |
| Coronary artery disease | Heart disease | C0010068 |
| Arm pain | Sore arm | C0003795 |
| Operative procedure of the knee | Knee surgery | C0187769 |
| | Family history of high blood pressure | CL103117 |
| | At risk for heart disease | CL200220 |
| | Knee ligament injury | CL111745 |
| sweat electrolytes | test for cystic fibrosis | C0428295 |

The concept unique identifiers and corresponding predefined health-related terms form a health terminology thesaurus that is stored on a computer-readable medium and provides the concept unique identifiers based upon the health-related terms. The consumer health terminology thesaurus incorporates terminology from many health-related vocabularies, including The Systematized Nomenclature of Medicine (SNOMED) promulgated by the College of American Pathologists and the International Classification of Diseases: 9th revision, Clinical Modification, promulgated by the Health Care Financing Administration, as well as the many consumer and lay medical terms created by WellMed, Inc. The thesaurus is an extension of the Unified Medical Language System (UMLS) Metathesaurus promulgated by the National Library of Medicine.

Figure 3:
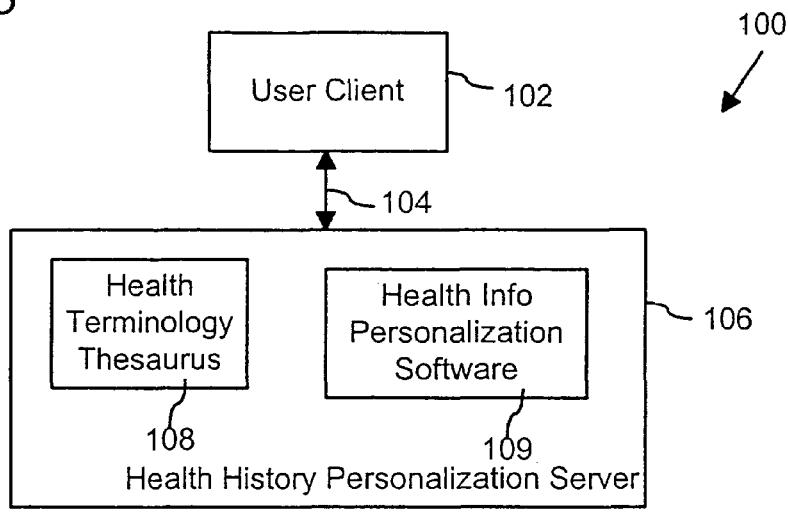
FIG. 3 is a block diagram of one implementation of a health history personalization computer system.

FIG. 3 is a block diagram of one implementation of a health history personalization computer system 100, which includes a user client 102 that communicates over a computer network 104 with a health history personalization server 106. Server 106 may be implemented as one or more server computers. In the case of multiple server computers, they may be local to each other or may be remote from each other and in communication via a computer network. User client 102 may be implemented as, for example, an interactive document or page that is accessible by the user at a client computer with conventional browser software.

Health history personalization server 106 stores a health terminology thesaurus 108 that correlates health terminology with concept unique identifiers. Health history personalization server 106 also includes health information personalization software 109 that cooperates with user client 102 for identifying the concept unique identifiers that correspond to personal health information (e.g., health conditions) specified by the user.

Figure 4:
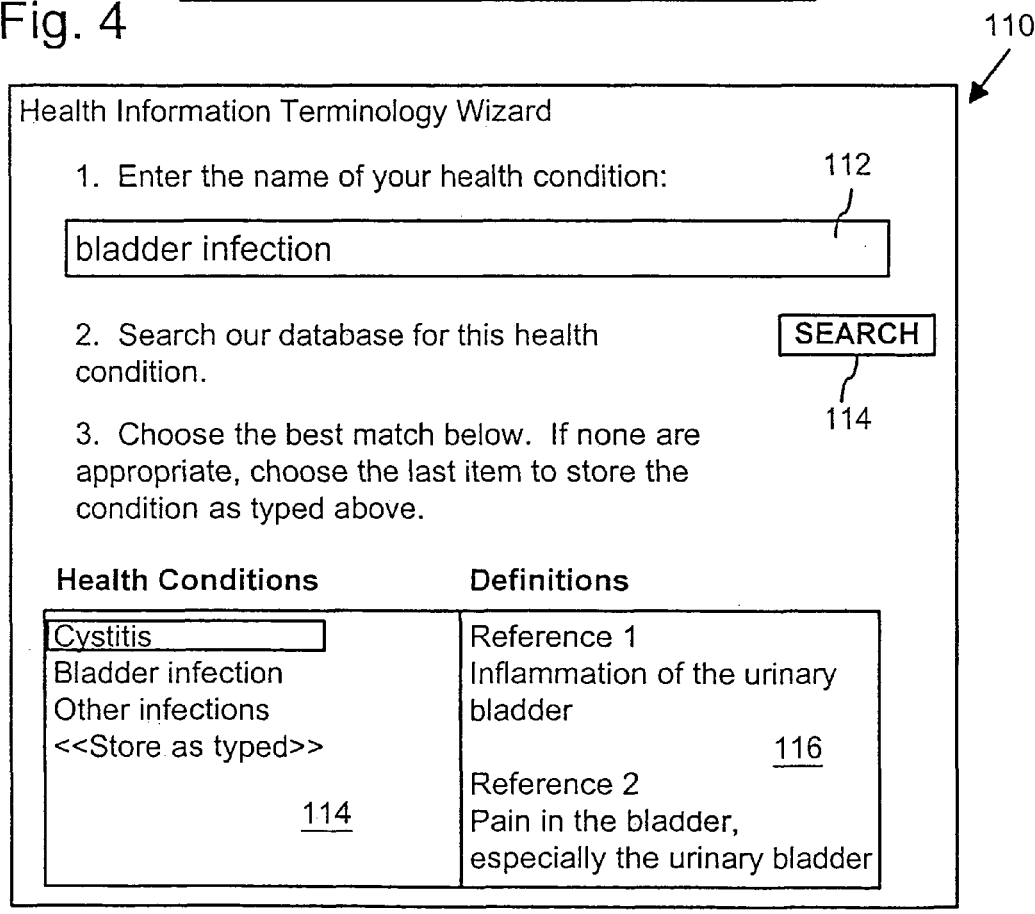
FIG. 4 is a diagrammatic illustration of a health information terminology wizard user interface.

FIG. 4 is a diagrammatic illustration of a health information terminology wizard user interface 110 that is rendered on a display screen for the user by user client 102. Health information terminology wizard user interface 110 assists a user in providing personal health information to health history personalization computer system 100.

User interface 110 includes a health information (e.g., health condition) entry pane 112 in which the user is prompted to enter a current or past health condition. A graphical control 114 allows the user to commence a search of health terminology thesaurus 108 for terms that are related or correspond to the health condition terminology the user entered into entry pane 112. In one implementation, the commencing of the search results in the health condition terminology entered by the user being transmitted over network 104 to health history personalization server 106 where thesaurus 108 is stored.

Any health terms that health information personalization software 109 identifies in thesaurus as 108 corresponding or relating to the information entered by the user are returned for display in a health terminology (e.g., health conditions) pane 114 of user interface 110. A prompt instructs the user to select one of the returned health terms that best corresponds to the user's health condition. Alternatively, the user may select an instruction to store the health information (e.g., health condition) as entered in entry pane 112. In one optional implementation, user interface 106 includes a definitions pane 116 in which text definitions may be provided for health terms selected by the user from health terminology pane 114 (e.g., cystitis in the illustration of FIG. 4). Health information personalization software 109 further includes a health terminology spell checking component that checks the spelling of terms entered by the user. In the event of apparent misspellings or unrecognized terms, server 106 returns to health terminology pane 114 one or more suggested correct spellings. Health history personalization server 106 correlates a concept unique identifier with the health term selected by the user as corresponding to the user's health condition, unless the user selects the instruction to store the health information (e.g., health condition) as typed in entry pane 112 rather than one of the returned matches. The concept unique identifier is stored at server 106 with identifying information regarding the user. When submitting a query in the entry pane 112, users may use a word related to the desired result. For example, the user may enter "heart" in the health conditions entry pane 112 to retrieve a list of health conditions having to do with the heart. Similarly, the user may enter "diabetes" to find all health conditions related to diabetes.

Also stored at server 106 are a listing of health-related content that is available over the network and concept unique identifiers indicative of the subject matter of the content. For example, server 106 could store a link or a network address for a news article entitled "Gene Identified As Cause Of Skin Disease" having associated with it the subject concepts of Xeroderma Pigmentosa (concept C0043345), skin cancer (concept C0007114), and genetic research (concept C0243064).

Server 106 correlates the user's personal health information (e.g., health conditions) with the corresponding health-related content. Server 106 identifies content having the same concept unique identifiers as those associated with the user's personal health information. For example, the news article entitled "Gene Identified As Cause Of Skin Disease" could be correlated with users who have Xeroderma Pigmentosa (concept C0043345), and users with skin cancer (concept C0007114). Links to the news article could be provided to both groups of users either in response to searches they conduct related to the specified topics, or the links may be delivered to the users automatically as a "push" of potentially relevant information identified at server 106.

As stated above with reference to FIG. 3, server 106 may be implemented as one or more server computers. In one implementation, thesaurus 108 resides on a first one or more server computers, personalization software 109 resides on a second one or more server computers, and the profiles of the individual users reside on a third one or more server computers.

Having described and illustrated the principles of our invention with reference to an illustrated embodiment, it will be recognized that the illustrated embodiment can be modified in arrangement and detail without departing from such principles. It should be understood that the programs, processes, or methods described herein are not related or limited to any particular type of computer apparatus, unless indicated otherwise. Various types of general purpose or specialized computer apparatus may be used with or perform operations in accordance with the teachings described herein. Elements of the illustrated embodiment shown in software may be implemented in hardware and vice versa.

In view of the many possible embodiments to which the principles of our invention may be applied, it should be recognized that the detailed embodiments are illustrative only and should not be taken as limiting the scope of our invention. Rather, we claim as our invention all such embodiments as may come within the scope and spirit of the following claims and equivalents thereto.

The invention claimed is:

1. A computer-implemented method comprising:
 receiving from a user health information about the user, said health information comprising health-related indicators of health conditions of the user;
 for the health-related indicators within the health information received about the user, identifying corresponding concept unique identifiers (CUIs) from an index that identifies relationships between CUIs and health-related indicators;
 storing in an electronic database information about a plurality of health-related works, wherein the plurality of health-related works includes works selected from the group consisting of health-related news and health-related articles;
 indexing the plurality of health-related works by a content index and a target population index, wherein the content index contains for each health-related work CUIs identifying the content of that health-related work and the target population index contains for each health-related work target information identifying populations of users for which that health-related work is appropriate;
 based at least in part upon said CUIs for the health-related indicators from the user, the CUIs within the content index for the plurality of health-related works, and the target information within the target index for the plurality of health-related works, identifying health-related works among the plurality of health-related works that are relevant to the user; and providing to the user access to the identified health-related works.

2. The method of claim 1, further comprising:
correlating each health-related work of the plurality of health-related works with a plurality of concept unique identifiers so that said each health-related work of the plurality of health-related works is characterized by a subset of CUIs selected from said plurality of concept unique identifiers.

3. The method of claim 1, further comprising:
providing a user interface to receive said health information about the user, wherein said user interface is configured to communicate with a computer server configured to verify said user's identity.

4. The method of claim 3, wherein said computer server is configured to process the health information from said user to identify any health-related indicators, and further, to identify all possible CUIs corresponding to said health-related indicators.

5. The method of claim 1, wherein identifying health-related works further comprises:
accessing one or more databases to obtain the plurality of health-related works, said one or more databases containing a variety of health-related literature.

6. The method of claim 5, wherein identifying health-related works further comprises:
for each health-related work of the plurality of health-related works, determining whether the CUIs associated with that health-related work contains at least one of the corresponding CUIs; and
responsive to determining that CUIs associated with one of the health-related works contains at least one of the corresponding CUIs, providing that health-related work to said user.

7. A computer system comprising:
a user interface configured for receiving from a user health information about the user, said health information comprising health-related indicators pertaining to personal health conditions; and
a processor in electronic communication with said user interface, said processor configured to execute computer instructions to perform the following functions:
for the health-related indicators within the health information received about the user, identifying corresponding concept unique identifiers (CUIs) from an index that identifies relationships between CUIs and health-related indicators, said index stored in a database accessible to said processor; and
accessing one or more online databases containing a plurality of health-related works, wherein the plurality of health-related works includes works selected from the group consisting of health-related news and health-related articles, wherein the plurality of health-related works are indexed by a content index and a target population index, wherein the content index contains for each health-related work CUIs identifying the content of that health-related work and the target population index contains for each health-related work target information identifying populations of users for which that health-related work is appropriate;
based at least in part upon said CUIs for the health-related indicators from the user, the CUIs within the content index for the plurality of health-related works, and the target information within the target index for the plurality of health-related works, identifying health-related works among the plurality of health-related works that are relevant to the user; and
providing to the user access to the identified health-related works.

8. The system of claim 7, wherein said processor is further configured to execute computer instructions to perform the following functions:
responsive to the identifying health-related works that are relevant to the user, sending said identified health-related works to said user.

9. The system of claim 8, wherein sending said identified health-related works are provided to said user by sending an email.

10. The system of claim 9, wherein sending an email involves sending either the content of said identified health-related works or a URL link for accessing the content of said identified health-related works.

11. The system of claim 7, wherein said processor is configured to access said one or more online databases containing a variety of health-related literature via a communication network.

12. The method of claim 1, wherein target information identifying populations of users for which that health-related work is appropriate does so by identifying populations of users for which that health-related work is not appropriate.

13. The system of claim 7, wherein target information identifying populations of users for which that health-related work is appropriate does so by identifying populations of users for which that health-related work is not appropriate.

14. The method of claim 1, wherein providing access involves providing hyperlinks to the identified health-related works to the user.

15. The system of claim 7, wherein providing access involves providing hyperlinks to the identified health-related works to the user.

16. The method of claim 1, wherein providing access involves sending the content of the identified health-related works to the user.

17. The system of claim 7, wherein providing access involves sending the content of the identified health-related works to the user.

* * * * *